US007384787B2

(12) United States Patent
Kazlauskas et al.

(10) Patent No.: US 7,384,787 B2
(45) Date of Patent: Jun. 10, 2008

(54) INCREASING PERHYDROLASE ACTIVITY IN ESTERASES AND/OR LIPASES

(75) Inventors: Romas Kazlauskas, Falcon Heights, MN (US); Peter Bernhardt, Cambridge, MA (US)

(73) Assignee: Regents of the University of Minnesota, Saint Paul, MN (US)

( * ) Notice: Subject to any disclaimer, the term of this patent is extended or adjusted under 35 U.S.C. 154(b) by 0 days.

(21) Appl. No.: 11/422,188

(22) Filed: Jun. 5, 2006

(65) Prior Publication Data

US 2006/0286651 A1 Dec. 21, 2006

Related U.S. Application Data

(60) Provisional application No. 60/687,679, filed on Jun. 6, 2005.

(51) Int. Cl.
*C12P 7/64* (2006.01)
*C12N 15/74* (2006.01)
*C12N 9/66* (2006.01)
*C07H 21/04* (2006.01)
*C12N 9/20* (2006.01)

(52) U.S. Cl. ............ 435/440; 435/218; 435/471; 435/198; 435/69.1; 435/134; 536/23.2

(58) Field of Classification Search ............ None
See application file for complete search history.

(56) References Cited

U.S. PATENT DOCUMENTS

| 5,108,457 A | 4/1992 | Poulose et al. |
| 5,352,594 A * | 10/1994 | Poulouse ............ 435/6 |
| 5,389,536 A | 2/1995 | Gray et al. |
| 2002/0128312 A1 | 9/2002 | Hei et al. |

FOREIGN PATENT DOCUMENTS

| DE | 102 60 903 | 7/2004 |
| WO | WO 99/67213 | 12/1999 |
| WO | WO 01/70030 | 9/2001 |
| WO | WO 03/066107 | 8/2003 |
| WO | WO 2004/058961 | 7/2004 |

OTHER PUBLICATIONS

Choi et al. Accession No. U12537, Genecore.*
GenBank Accession No. AAN69615 dated Jan. 10, 2006, 2 pages.
GenBank Accession No. AAP10065 dated Dec. 30, 2005, 2 pages.
GenBank Accession No. AF031153 dated Nov. 18, 1997, 2 pages.
GenBank Accession No. AF031242 dated Nov. 20, 1997, 2 pages.
GenBank Accession No. BAA10684 dated May 20, 2006, 2 pages.
GenBank Accession No. BAC55927 dated Jan. 28, 2003, 2 pages.
GenBank Accession No. D50587 dated Sep. 23, 2006, 2 pages.
GenBank Accession No. J04167 dated Apr. 26, 1993, 4 pages.
GenBank Accession No. L24749 dated Jul. 14, 1994, 2 pages.
GenBank Accession No. L26319 dated Dec. 10, 1994, 2 pages.
GenBank Accession No. M19677 dated Apr. 27, 1993, 2 pages.
GenBank Accession No. M35302 dated Apr. 27, 1993, 2 pages.
GenBank Accession No. M68491 dated Apr. 26, 1993, 2 pages.
GenBank Accession No. M74010 dated Apr. 26, 1993, 2 pages.
GenBank Accession No. M84990 dated Nov. 14, 1997, 2 pages.
GenBank Accession No. P19076 dated Dec. 12, 2006, 2 pages.
GenBank Accession No. P23133 dated Oct. 17, 2006, 2 pages.
GenBank Accession No. U01096 dated Aug. 6, 1994, 3 pages.
GenBank Accession No. U02635 dated Jun. 6, 1994, 2 pages.
GenBank Accession No. U12537 dated Aug. 22, 1995, 3 pages.
GenBank Accession No. X17366 dated Apr. 18, 2005, 2 pages.
GenBank Accession No. X54516 dated Apr. 18, 2005, 2 pages.
GenBank Accession No. X61673 dated Apr. 18, 2005, 2 pages.
GenBank Accession No. X66104 dated Nov. 14, 2006, 3 pages.
"Bleaching With Sodium Perborate" [online]. Borax, 2003, [retrieved on Feb. 25, 2005]. Retrieved from the Internet: <URL: www.borax.com/detergents/bleaching_2.html>, 2 pages.
"Environmentally Beneficial Biocatalysis" Biocat Update, 2005, The Center for Biocatalysis and Bioprocessing—The University of Iowa, 12(1):1-7.
Blow, "More of the catalytic triad," *Nature*, 1990, 343:694-695.
Cheeseman et al., "Structure of an aryl esterase from *Pseudomonas fluorescens*" *Acta Cryst.*, 2004, D60:1237-1243.
Drabløs & Petersen, "Identification of Conserved Residues in Family of Esterase and Lipase Sequences," *Meth. Enzymol.*, 1997, 284:28-61.
Fatemi & Frank, "Inactivation of *Listeria monocytogenes*/ *Pseudomonas* Biofilms by Peracid Sanitizers," *J. Food Protect.*, 1999, 62(7):761-765.
Fersht et al., "Hydrogen bonding and biological specificity analysed by protein engineering," *Nature*, 1985, 314:235-238.
Fersht, "Relationships between Apparent Binding Energies Measured in Site-Directed Mutagenesis Experiments and Energetics of Binding and Catalysis," *Biochemistry*, 1988, 27:1577-1580.
Hager et al., "Chloroperoxidase. II. Utilization of Halogen Anions," *J. Biol. Chem.*, 1966, 241(8):1769-1777.
Hofmann et al., "Structural Investigation of the Cofactor-free Chloroperoxidases," *J. Mol. Biol.*, 1998, 279:889-900.
Lau, "The use of lipases in non-natural reactions," Delft University of Technology, Department of Biotechnology, Biocatalysis and Organic Chemistry Group, Project term: Jan. 1999-Jan. 2003, located at http://www.bt.tudelft.nl/live/binaries/c3a87339-4e34-4320-9790-04e8a233385d/doc/BOCprLau.pdf, 1 page.

* cited by examiner

*Primary Examiner*—Rebecca Prouty
*Assistant Examiner*—Younus Meah
(74) *Attorney, Agent, or Firm*—Fish & Richardson P.C.

(57) ABSTRACT

The invention provides for methods of modifying n esterase or a lipase enzyme to introduce perhydrolase activity or to increase the already-existing perhydrolase activity. The invention also provides for methods of converting an polypeptide having predominantly esterase and/or lipase catalytic activity to a polypeptide having predominantly perhydrolase activity.

7 Claims, 1 Drawing Sheet

SEQUENCE LISTING

```
<160> NUMBER OF SEQ ID NOS: 4

<210> SEQ ID NO 1
<211> LENGTH: 1202
<212> TYPE: DNA
<213> ORGANISM: Pseudomonas fluorescens
<220> FEATURE:
<223> OTHER INFORMATION: esterase

<400> SEQUENCE: 1
gatctggacg tcctcggccc ccggcgcgcg gcgtcgaagg tgaagggctt gagggcatcc      60
ttggcgttct gggcggcgta gctgtaagtc ttggccattt cgttcacctg tgtgatctga     120
cggtagaggt cagtggacca gcatagacgc tgaaccgttc aaccgagcac accggtacaa     180
gcccttcgtc cggtttcacg caatagtgcg ctagagtctt tcagcccct caaccaggag      240 tttttgcatg agcacatttg ttgcaaaaga cggtacccag atctatttca aggactgggg      300
```

-continued

| | |
|---|---|
| cagcggtaaa ccggtgttgt tcagccacgg ttggctactg gatgccgaca tgtgggaata | 360 |
| ccagatggag tacctcagca gccgcggcta tcgcaccatc gcctttgacc gccgcggctt | 420 |
| tggccgctcg gaccaaccct ggaccggcaa cgactacgac accttcgccg acgacatcgc | 480 |
| ccagttgatc gaacacctgg acctcaagga ggtgaccctg gtgggcttct ccatgggcgg | 540 |
| cggcgatgtg gcccgctaca tcgcccgcca cggcagcgca cgggtggccg gcctggtgct | 600 |
| gctgggcgcc gtcaccccgc tgttcggcca gaagcccgac tatccgcagg gtgtcccgct | 660 |
| cgatgtgttc gcaaggttca agactgagct gctgaaggat cgcgcgcagt tcatcagcga | 720 |
| tttcaacgca ccgttctatg gcatcaacaa gggccaggtc gtctcccaag gcgtgcagac | 780 |
| ccagaccctg caaatcgccc tgctggcctc gctcaaggcc acggtggatt gcgtcaccgc | 840 |
| gttcgccgaa accgacttcc gcccggacat ggccaagatc gacgtaccca ccctggtgat | 900 |
| ccatggcgat ggcgaccaga tcgtgccgtt cgagaccacc ggcaaagtgg cggcggagtt | 960 |
| gatcaagggc gccgaactga aggtgtacaa ggacgcgccc cacgggttcg cggtgaccca | 1020 |
| cgcccagcag ttgaacgaag acctgttggc gttcttgaaa cgctgagtta atgtctgcct | 1080 |
| ttatcggccg ggcttgcccg gcctttttt tacgcgctcg aatctcgcgc ggtcgccggg | 1140 |
| cacgatcgtg ctgaaccgcc gccccctcgc cacggtccca acccatacgt tcatcgctgc | 1200 |
| ag | 1202 |

```
<210> SEQ ID NO 2
<211> LENGTH: 1029
<212> TYPE: DNA
<213> ORGANISM: Candida antarctica
<220> FEATURE:
<223> OTHER INFORMATION: lipase

<400> SEQUENCE: 2
```

| | |
|---|---|
| atgaagctac tctctctgac cggtgtggct ggtgtgcttg cgacttgcgt tgcagccact | 60 |
| cctttggtga agcgtctacc ttccggttcg gaccctgcct tttcgcagcc caagtcggtg | 120 |
| ctcgatgcgg gtctgacctg ccagggtgct tcgccatcct cggtctccaa acccatcctt | 180 |
| ctcgtccccg gaaccggcac cacaggtcca cagtcgttcg actcgaactg gatccccctc | 240 |
| tcaacgcagt tgggttacac accctgctgg atctcacccc cgccgttcat gctcaacgac | 300 |
| acccaggtca acacggagta catggtcaac gccatcaccg cgctctacgc tggttcgggc | 360 |
| aacaacaagc ttcccgtgct tacctggtcc caggtggtc tggttgcaca gtggggtctg | 420 |
| accttcttcc ccagtatcag gtccaaggtc gatcgactta tggcctttgc gcccgactac | 480 |
| aagggcaccg tcctcgccgg ccctctcgat gcactcgcgg ttagtgcacc ctccgtatgg | 540 |
| cagcaaacca ccggttcggc actcaccacc gcactccgaa acgcaggtgg tctgacccag | 600 |
| atcgtgccca ccaccaacct ctactcggcg accgacgaga tcgttcagcc tcaggtgtcc | 660 |
| aactcgccac tcgactcatc ctacctcttc aacggaaaga acgtccaggc acaggccgtg | 720 |
| tgtgggccgc tgttcgtcat cgaccatgca ggctcgctca cctcgcagtt ctcctacgtc | 780 |
| gtcggtcgat ccgccctgcg ctccaccacg ggccaggctc gtagtgcaga ctatggcatt | 840 |
| acggactgca acctcttcc cgccaatgat ctgactcccg agcaaaaggt cgccgcggct | 900 |
| gcgctcctgg cgccggcagc tgcagccatc gtggcgggtc caaagcagaa ctgcgagccc | 960 |
| gacctcatgc cctacgcccg cccctttgca gtaggcaaaa ggacctgctc cggcatcgtc | 1020 |
| acccctga | 1029 |

```
<210> SEQ ID NO 3
<211> LENGTH: 272
<212> TYPE: PRT
<213> ORGANISM: Pseudomonas fluorescens
<220> FEATURE:
<223> OTHER INFORMATION: esterase

<400> SEQUENCE: 3

Met Ser Thr Phe Val Ala Lys Asp Gly Thr Gln Ile Tyr Phe Lys Asp
 1               5                  10                  15

Trp Gly Ser Gly Lys Pro Val Leu Phe Ser His Gly Trp Leu Leu Asp
                20                  25                  30

Ala Asp Met Trp Glu Tyr Gln Met Glu Tyr Leu Ser Ser Arg Gly Tyr
            35                  40                  45

Arg Thr Ile Ala Phe Asp Arg Arg Gly Phe Gly Arg Ser Asp Gln Pro
        50                  55                  60

Trp Thr Gly Asn Asp Tyr Asp Thr Phe Ala Asp Asp Ile Ala Gln Leu
65                  70                  75                  80

Ile Glu His Leu Asp Leu Lys Glu Val Thr Leu Val Gly Phe Ser Met
                85                  90                  95

Gly Gly Gly Asp Val Ala Arg Tyr Ile Ala Arg His Gly Ser Ala Arg
            100                 105                 110

Val Ala Gly Leu Val Leu Leu Gly Ala Val Thr Pro Leu Phe Gly Gln
        115                 120                 125

Lys Pro Asp Tyr Pro Gln Gly Val Pro Leu Asp Val Phe Ala Arg Phe
    130                 135                 140

Lys Thr Glu Leu Leu Lys Asp Arg Ala Gln Phe Ile Ser Asp Phe Asn
145                 150                 155                 160

Ala Pro Phe Tyr Gly Ile Asn Lys Gly Gln Val Val Ser Gln Gly Val
                165                 170                 175

Gln Thr Gln Thr Leu Gln Ile Ala Leu Leu Ala Ser Leu Lys Ala Thr
            180                 185                 190

Val Asp Cys Val Thr Ala Phe Ala Glu Thr Asp Phe Arg Pro Asp Met
        195                 200                 205

Ala Lys Ile Asp Val Pro Thr Leu Val Ile His Gly Asp Gly Asp Gln
    210                 215                 220

Ile Val Pro Phe Glu Thr Thr Gly Lys Val Ala Ala Glu Leu Ile Lys
225                 230                 235                 240

Gly Ala Glu Leu Lys Val Tyr Lys Asp Ala Pro His Gly Phe Ala Val
                245                 250                 255

Thr His Ala Gln Gln Leu Asn Glu Asp Leu Leu Ala Phe Leu Lys Arg
            260                 265                 270

<210> SEQ ID NO 4
<211> LENGTH: 317
<212> TYPE: PRT
<213> ORGANISM: Candida antarctica
<220> FEATURE:
<223> OTHER INFORMATION: lipase

<400> SEQUENCE: 4

Leu Pro Ser Gly Ser Asp Pro Ala Phe Ser Gln Pro Lys Ser Val Leu
 1               5                  10                  15

Asp Ala Gly Leu Thr Cys Gln Gly Ala Ser Pro Ser Ser Val Ser Lys
                20                  25                  30

Pro Ile Leu Leu Val Pro Gly Thr Gly Thr Thr Gly Pro Gln Ser Phe
            35                  40                  45
```

-continued

```
Asp Ser Asn Trp Ile Pro Leu Ser Thr Gln Leu Gly Tyr Thr Pro Cys
    50                  55                  60

Trp Ile Ser Pro Pro Pro Phe Met Leu Asn Asp Thr Gln Val Asn Thr
65              70                  75                      80

Glu Tyr Met Val Asn Ala Ile Thr Ala Leu Tyr Ala Gly Ser Gly Asn
                85                  90                  95

Asn Lys Leu Pro Val Leu Thr Trp Ser Gln Gly Gly Leu Val Ala Gln
            100                 105                 110

Trp Gly Leu Thr Phe Phe Pro Ser Ile Arg Ser Lys Val Asp Arg Leu
            115                 120                 125

Met Ala Phe Ala Pro Asp Tyr Lys Gly Thr Val Leu Ala Gly Pro Leu
    130                 135                 140

Asp Ala Leu Ala Val Ser Ala Pro Ser Val Trp Gln Gln Thr Thr Gly
145             150                 155                     160

Ser Ala Leu Thr Thr Ala Leu Arg Asn Ala Gly Gly Leu Thr Gln Ile
            165                 170                 175

Val Pro Thr Thr Asn Leu Tyr Ser Ala Thr Asp Glu Ile Val Gln Pro
            180                 185                 190

Gln Val Ser Asn Ser Pro Leu Asp Ser Ser Tyr Leu Phe Asn Gly Lys
        195                 200                 205

Asn Val Gln Ala Gln Ala Val Cys Gly Pro Leu Phe Val Ile Asp His
    210                 215                 220

Ala Gly Ser Leu Thr Ser Gln Phe Ser Tyr Val Val Gly Arg Ser Ala
225             230                 235                     240

Leu Arg Ser Thr Thr Gly Gln Ala Arg Ser Ala Asp Tyr Gly Ile Thr
            245                 250                 255

Asp Cys Asn Pro Leu Pro Ala Asn Asp Leu Thr Pro Glu Gln Lys Val
            260                 265                 270

Ala Ala Ala Ala Leu Leu Ala Pro Ala Ala Ala Ile Val Ala Gly
            275                 280                 285

Pro Lys Gln Asn Cys Glu Pro Asp Leu Met Pro Tyr Ala Arg Pro Phe
    290                 295                 300

Ala Val Gly Lys Arg Thr Cys Ser Gly Ile Val Thr Pro
305             310                 315
```

INCREASING PERHYDROLASE ACTIVITY IN ESTERASES AND/OR LIPASES

CROSS-REFERENCE TO RELATED APPLICATIONS

This application claims priority under 35 U.S.C. §119(e) of U.S. application Ser. No. 60/687,679, filed Jun. 6, 2005.

TECHNICAL FIELD

This invention relates to enzymes, and more particularly to increasing perhydrolase activity in esterases and/or lipases.

BACKGROUND

Catalytic promiscuity is the ability of the active site of one enzyme to catalyze several chemical transformations. Understanding and controlling catalytic promiscuity are key to understanding the evolution of new enzymatic activity and to design new enzyme-catalyzed reactions for synthesis. The rationale presented here, which was used to increase the perhydrolase activity in an esterase or a lipase, may be used to design other enzymes with altered nucleophile selectivity and to catalyze stereoselective oxidations.

SUMMARY

The invention provides for methods of modifying an esterase or a lipase enzyme to introduce perhydrolase activity or to increase the already-existing perhydrolase activity. The invention also provides for methods of converting an polypeptide having predominantly esterase and/or lipase catalytic activity to a polypeptide having predominantly perhydrolase activity.

In one aspect, the invention provides methods of increasing perhydrolase activity in an esterase or lipase. Such methods generally include providing a nucleic acid encoding the esterase or lipase, modifying one or more nucleotides in the codon encoding the OXY+1 residue in the esterase or lipase to nucleotides that cause the codon to encode an amino acid that can adopt a cis-configuration, and expressing the modified nucleic acid to generate a modified polypeptide, wherein the modified polypeptide has increased perhydrolase activity compared to the pre-modified esterase or lipase. Such a method also can include screening the esterase or lipase for perhydrolase activity and/or screening the modified polypeptide for perhydrolase activity.

A representative amino acid that can adopt a cis-configuration is proline or a derivative of proline (e.g., hydroxyproline). A representative nucleic acid encoding an esterase has the sequence shown in SEQ ID NO:1, and a representative nucleic acid encoding a lipase has the sequence shown in SEQ ID NO:2. Generally, an esterase or lipase suitable for use in the invention is a bacterial esterase or lipase, a fungal esterase or lipase, a mammalian esterase or lipase, or a plant esterase or lipase.

In another aspect, the invention provides methods of introducing perhydrolase activity into an esterase or lipase. Such methods generally include providing a nucleic acid encoding the esterase or lipase, modifying one or more nucleotides in the codon encoding the OXY+1 residue in the esterase or lipase to nucleotides that cause the codon to encode an amino acid that can adopt a cis-configuration, and expressing the modified nucleic acid to generate a modified polypeptide, wherein the modified polypeptide has perhydrolase activity.

In still another aspect, the invention provides methods of converting a polypeptide having predominantly esterase and/or lipase activity to a polypeptide having predominantly perhydrolase activity. Such methods generally include providing a nucleic acid encoding the polypeptide having predominantly esterase and/or lipase activity, modifying one or more nucleotides in the codon encoding the OXY+1 residue in the polypeptide to nucleotides that cause the codon to encode an amino acid that can adopt a cis-configuration, and expressing the modified nucleic acid to generate a modified polypeptide, wherein the modified polypeptide has predominantly perhydrolase activity.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

Like reference symbols in the various drawings indicate like elements.

DETAILED DESCRIPTION

The invention provides for methods of modifying an esterase or a lipase enzyme to introduce perhydrolase activity into the enzyme or to increase the already-existing perhydrolase activity. The invention also provides for methods of converting a polypeptide having predominantly esterase and/or lipase catalytic activity to a polypeptide having predominantly perhydrolase activity. It is shown herein that substituting a single amino acid in PFE was sufficient to shift the activity from hydrolysis to perhydrolysis in aqueous solution. The perhydrolase activity is similar to that of naturally occurring perhydrolases.

This disclosure provides methods for increasing the existing perhydrolase activity in an esterase or lipase, and methods for introducing novel perhydrolase activity into an esterase or lipase. This disclosure further provides methods of converting a polypeptide having predominantly esterase and/or lipase activity into a polypeptide having predominantly perhydrolase activity.

Perhydrolases, esterases, and lipases all contain a catalytic triad consisting of a Serine (Ser), a Glutamate (Glu) or Aspartate (Asp), and a Histidine (His). See, for example, Blow, 1990, *Nature,* 343:694-5. Perhydrolases (previously known as metal-free haloperoxidases) contain a Ser-His-Asp catalytic triad and catalyze the reversible formation of peracid from hydrogen peroxide and carboxylic acids [Eq. (1)].

Perhydrolysis presumably takes place with an esterase-like mechanism in which a carboxylic acid reacts with the active site serine to form an acyl enzyme intermediate, which then reacts with hydrogen peroxide to form a peracid. The change from water to hydrogen peroxide as a nucleophile could be considered a change in substrate selectivity, but the very different chemical reactivity of the products (carboxylic acid vs. peroxy-carboxylic acid) makes this an example of alternate catalytic activity. Recent X-ray structures of an aryl esterase from *Pseudomonas fluorescens* (PFE), which shows low perhydrolase activity, and a homologous perhydrolase from *P. fluorescens* (CPO—F) show very similar active sites and no obvious structural basis for esterase vs. perhydrolase activity. See, for example, Cheeseman et al., 2004, *Acta Crystallogr. Sect. D: Biol. Crystallogr.*, 60:1237-43.

Among the different types of esterase enzymes are those that act on carboxylic esters (EC 3.1.1). The consensus pattern for carboxyl-esterases is F-[GR]-G-x(4)-[LIVM]-x-[LIV]-x-G-x-S-[STAG]-G, wherein S is the active site residue (ProSite Documentation PDOC00112; for information regarding ProSite prefixes, see Sonhammer et al., 1997, *Protein*, 28:405-420 or expasy.org on the World Wide Web). See, also, Myers et al., 1988, *Mol. Biol. Evol.*, 5:113-9; Krejci et al., 1991, *PNAS USA*, 88:6647-51; and Drablos & Petersen, 1997, *Methods in Enzymol.*, 284:28-61. The nucleic acid sequence of a representative esterase is shown in SEQ ID NO: 1, and the encoded amino acid sequence is shown in SEQ ID NO:3. The sequences of additional representative esterases can be found, for example, at GenBank Accession Nos. X66104, L26319, M19677, J04167, M68491, and L24749.

Lipases are widely distributed in animals, plants, and prokaryotes. Triglyceride lipases (EC 3.1.1.3) are lipolytic enzymes that hydrolyse ester linkages of triglycerides. The consensus pattern of lipases is [LIV]-{KG}-[LIVFY]-[LIVMST]-G-[HYWV]-S-{YAG}-G-[GSTAC], wherein S is the active site residue (ProSite Documentation PDOC00110; for information regarding ProSite prefixes, see Sonhammer et al., 1997, *Protein*, 28:405-420 or expasy.org on the World Wide Web). See, also, Persson et al., 1989, *Eur. J. Biochem.*, 179:39-45; and Drablos & Petersen, 1997, *Methods in Enzymol.*, 284:28-61. The nucleic acid sequence of a representative lipase is shown in SEQ ID NO:2, and the encoded amino acid sequence is shown in SEQ ID NO:4. The sequences of additional representative lipases can be found, for example, at GenBank Accession Nos. X61673, D50587, X17366, X54516, M35302 and M74010.

In order to increase the perhydrolase activity in an esterase or lipase, to introduce perhydrolase activity into an esterase or lipase, or to convert a polypeptide having predominantly esterase and/or lipase activity to a polypeptide having predominantly perhydrolase activity, one or more nucleotides in the esterase or lipase are modified. Nucleic acids suitable for use as starting materials in the methods disclosed herein include nucleic acids encoding bacterial esterases or lipases, fungal esterases or lipases, mammalian esterases or lipases, or plant esterases or lipases. Other enzymes that perform hydrolysis reactions may be suitable for modification by the methods of the invention.

Generally, nucleotides that encode the OXY+1 residue are identified in the esterase or lipase and modified to encode an amino acid that can adopt a cis-configuration. In addition to modifying the OXY+1 residue, nucleotides encoding any one or more of the other 13 residues identified herein also can be modified in an esterase or lipase to increase or introduce perhydrolase activity.

The OXY+1 residue can be identified from 3-D modeling of the polypeptide. The loop regions containing the active site residues that form the catalytic Ser-His-Asp/Glu triad and a fourth, short loop that reaches near the active site can be identified. This fourth, short loop usually comprises amino acids from the N-terminus of the polypeptide and contains the carbonyl oxygen involved in perhydrolase activity. The carbonyl oxygen is attached to the residue forming the oxyanion hole (referred to herein as the "OXY" residue). Modification of the first residue on the carboxy side of the oxyanion hole residue (referred to herein as the "OXY+1" residue), alone and/or in combination with other mutations, imparts increased perhydrolase activity to the polypeptide.

Although not bound by any particular mechanism, it is suggested herein that a carbonyl group in the vicinity of the active site serves as a stabilizer for hydrogen peroxide attack on a putative acyl-enzyme intermediate, which ultimately results in an increase in perhydrolase activity. Therefore, in addition to, or as an alternative to, modifying the OXY+1 residue as described above, modifications at one or more other residues (e.g., one or more of the remaining 13 residues identified herein) can be introduced into the polypeptide and the modified polypeptide modelled. The distance between the O$\gamma$ and the C=O is measured. As discussed below, a distance between the O$\gamma$ and the C=O that is closer to 2.7 Å rather than 3.2 Å appears to provide stability to facilitate optimal perhydrolase activity. Although not bound by any particular mechanism, the distance between the catalytic serine O$\gamma$ atom and the carbonyl oxygen (C=O) is an indication of hydrogen bond strength. Typically, this distance is 2.8±0.1 Å. A distance exceeding this value is considered a very weak to an absent hydrogen bond, which would provide little to no stability and cause sub-optimal perhydrolase activity.

A number of computer programs are available and known in the art for 3-D modeling of polypeptides. For example, InsightII (Accelrys, San Diego, Calif.) and Sybyl (Tripos, St. Louis, Mo.). Standard protocols for energy minimization and computer modeling are known to those of skill in this art. See, for example, Leach, Molecular Modeling: Theory and Applications, 2$^{nd}$ Ed., Prentice Hall, 2001.

Amino acids that can adopt a cis-configuration can be a natural or a non-natural amino acid. A non-limiting representative example of an amino acid that can adopt a cis-configuration is proline or a proline derivative such as hydroxyproline. Other amino acids including aspartate, asparagine, alanine, phenylalanine, glutamate, glycine, serine, tyrosine, threonine, histidine, and tryptophan are able to adopt a cis-configuration. A review of cis-forming amino acid residues, can be found, for example, on the World Wide Web at imb-jena.de/ImgLibDoc/cispep/non_proline/IMAGE_CISPEP2.html.

One or more nucleotides encoding a particular amino acid residue in a polypeptide can be modified using a number of different methods known in the art. For example, site-directed mutagenesis can be used to modify one or more nucleotides such that those codons encode an amino acid residue that differs from the corresponding residue encoded by the wild-type polypeptide. One of the most common methods of site-directed mutagenesis is oligonucleotide-directed mutagenesis. In oligonucleotide-directed mutagenesis, an oligonucleotide encoding the desired mutation(s) is annealed to one strand of the DNA of interest and serves as a primer for initiation of DNA synthesis. In this manner, the mutagenic oligonucleotide is incorporated into the newly synthesized strand. See, for example, Lewis & Thompson, 1990, *Nucl. Acids Res.*, 18:3439; Bohnsack, 1996, *Meth. Mol. Biol*, 57:1; Vavra & Brondyk, 1996, *Promega Notes*, 58:30; Deng & Nickoloff, 1992, *Anal. Biochem.*, 200:81; Kunkel, 1985, *Proc. Natl. Acad. Sci. USA*, 82:488; Kunkel et al., 1987, *Meth. Enzymol.*, 154:367; Taylor et al., 1985, *Nucl. Acids Res.*, 13:8764; Nakamaye & Eckstein, 1986, *Nucl. Acids Res.*, 14:9679; Higuchi et al., 1988, *Nucl. Acids Res.*, 16:7351; Shimada, 1996, *Meth. Mol. Biol.*, 57:157; Ho et al., 1989, *Gene*, 77:51; Horton et al., 1989, *Gene*, 77:61; Sarkar & Sommer, 1990, *BioTechniques*, 8:404.

Other methods are used routinely in the art to modify the sequence of a protein or polypeptide. For example, polypeptides can be chemically synthesized to have the desired modified amino acid sequence. See, for example, Bang & Kent, 2005, *PNAS USA*, 102:5014-9 and references therein. In addition, nucleic acids can be generated (e.g., by PCR) and expressed to produce a modified or an unmodified polypeptide.

Methods for evaluating the catalytic activity of enzymes are used routinely in the art. Esterase activity, lipase activity, and/or perhydrolase activity of a modified or un-modified polypeptide can be evaluated using known methods. For example, esterase activity can be evaluated using the hydrolysis of p-nitrophenyl acetate (pNPAc); lipase activity can be evaluated using p-nitrophenyl palmitate (PNPP); and perhydrolase activity can be evaluated using a monochlorodimedone (MCD) assay. See, for example, Hager et al., 1966, *J. Biol. Chem.*, 241:1769-77.

The modified enzymes made by the methods disclosed herein can be used, for example, in detergents. Modified enzymes that exhibit perhydrolase activity can be used, for example, in laundry detergents to remove fat stains from fabrics. Modified enzymes that have perhydrolase activity also can be used in industrial sanitary and waste treatment applications. Industries such as textiles and pulp and paper are increasingly using peroxide in bleaching processes, and need an environmentally friendly process to de-toxify the waste resulting therefrom.

The modified enzymes made by the methods disclosed herein also can be used to make derivatives of peracid (e.g., peroxycarboxylic acid). Peroxycarboxylic acid in various formulations can disinfect, and eliminate biofilms and microbial contamination. See, for example, U.S. Publication No. 2002128312; PCT Publication No. WO 2003066107; PCT Publication No. WO 2001070030; and PCT Publication No. WO 9967213. For example, Fatemi & Frank (1999, *J. Food Protect.*, 62:761-5) removed biofilms from food processing equipment within a minute using 160 parts per million peroxycarboxylic acids. Current chemical methods for making peroxycarboxylic acids usually involve very acidic, harsh conditions. An enzymatic method of making peroxycarboxylic acids would be beneficial to industry and to the environment.

Commercially useful lipases and esterases include, but are not limited to, *Candida antarctica* lipase B (CALB), *Humicola lanuginosa* lipase (HLL), *Pseudomonas cepacia* lipase (PCL), *Candida rugosa* lipase (CRL), Pig-liver esterase (PLE), *Mucor javanicus* lipase (MJL), *Mucor miehi* lipase (MML), and *Bacillus thermocateriualatus* esterase (BTE). Crystal structures have been determined for CALB (PDB ID: 1TCA), HLL (PDB ID: 1DT5), PCL (PDB ID: 1OIL), and CRL (PDB ID: 1GZ7).

Once it has been determined that a modified enzyme has perhydrolase activity, the enzyme can be evaluated at various pHs and/or temperatures for activity. Enzyme production can be established at industrially-relevant volumes using techniques known in the art (e.g., fermentation). For applications in which a modified enzyme is being used, for example, to de-toxify waste liquids, the modified enzyme can be attached to polymer beads and packed into columns for filtering the waste.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the invention described in the claims.

EXAMPLES

Example 1

Identification of Residues Important to Perhydrolase Activity

Previous experiments to convert PFE into a perhydrolase focused on three amino acids that differ between PFE and CPO-F (Met95, 4.5 Å from Ser94 Oγ to Met 95 Cα; Tyr69, 14 Å; and Thr122, 9.9 Å). Mutations at these sites did not significantly change perhydrolase activity. The Met95Thr mutation decreased esterase activity from 13.7 to 3.4 U mg$^{-1}$ and decreased perhydrolase activity to below the detection limit (<0.02 U mg$^{-1}$). 1 U is equivalent to the consumption of 1 μmol of substrate min$^{-1}$. This decrease may be due to a shift in the backbone amide of residue 95, which forms part of the oxyanion hole. The esterase and perhydrolase activities of Tyr69Met and Thr122Pro are very similar to those for the wild-type protein (Table 1).

Since a direct structural comparison of PFE and CPO-F did not reveal how to increase perhydrolase activity, amino acid sequence alignments (ClustalW) of several hydrolases and perhydrolases were used to identify the essential residues for each activity. There were not enough aryl esterase sequences available in the databases so the set was expanded to serine hydrolases, which are still homologous. The sequences used were CPO-F from *P. fluorescens* (GenBank Accession No. AF031153); BPO-A1 from *Streptomyces aureofaciens* (GenBank Accession No. U01096); CPO-L from *Streptomyces lividans* (GenBank Accession No. U02635); CPO from *S. aureofaciens* (GenBank Accession No. AF031242); BPO-A2 from *S. aureofaciens* (GenBank Accession No. M84990); BPO from *Synechocystis* sp (GenBank Accession No. BAA10684); aryl esterase from *P. fluorescens* (GenBank Accession No. U12537); aryl esterase from *Bacillus cereus* (GenBank Accession No. AAP10065); esterase from *Pseudomonas putida* (GenBank Accession No. AAN69615); dihydrocoumarin hydrolase from *Actinobacter calcoaceticus* (GenBank Accession No. BAC55927); 2-hydroxy-6-oxohepta-2,4-dienoate hydrolase from *P. putida* (GenBank Accession No. P23133); and 2-hydroxymuconic semialdehyde hydrolase from *P. putida* (GenBank Accession No. P19076).

Comparison of these six esterase and six perhydrolase sequences identified fifteen amino acids common to most esterases and fifty-seven amino acids common to most perhydrolases. A Venn diagram (Rothman and Kirsch, 2003, *J. Mol. Biol.*, 327:593-608) was used to map residues conserved in esterases but no in perhydrolases, in esterases and perhydrolases, and in perhydrolases but not in esterases. PFE contains most of the amino acid residues common to esterases. PFE, however, has amino acid substitutions at fourteen positions out of the fifty-seven amino acids common to most perhydrolases. Perhydrolases generally contain the following residues at the indicated position. The residue in parentheses is the corresponding residue present in PFE. Thr4 (Val), Tyr13 (Phe), Val23 (Leu), Pro29 (Leu29), Leu76 (Ile), Glu99 (Asp), Lys114 (Gly), Lys127 (Gln), Asn131 (Tyr), Glu138 (Asp), Asp141 (Ala), Trp182 (Ile), Ile227 (Phe), and Gly248 (Asp).

It was hypothesized that an increase in perhydrolase activity and a decrease in esterase activity of an enzyme could be achieved by substituting one or several of the fourteen amino acid residues identified. It was further hypothesized that the residues closer to the active site (in a three-dimensional configuration and not necessarily in the linear sequence) are more important for catalytic activity than residues more distal to the active site. Therefore, distances between the conserved residue's Cα and the catalytic serine's Oγ were measured (see below). Three amino acid residues were within a 12 Å sphere of the catalytic Ser94 Oγ: proline at position 29 (Pro29), glutamic acid at position 99 (Glu99), and isoleucine at position 227 (Ile227).

Site-directed mutagenesis using complementary, mutagenic PCR-primers yielded the Leu29Pro, Asp99Glu, and Phe227Ile mutants of PFE. DNA sequencing confirmed the mutations and protein were expressed and purified as described (Cheeseman et al., 2004, *Acta Crystallogr. Sect. D: Biol. Crystallogr.*, 60:1237-1243).

Example 2

Methods of Evaluating Enzyme Activity

Activity assays were performed in quadruplicates on 96-well microtiter plates with a reaction volume of 100 μl (90 μl assay solution to 10 μl enzyme in 5 mM BES pH 7.2). The path-length for light through the well was 0.29 cm.

The monochlorodimedon (MCD) assay (Hager et al., 1966, *J. Biol. Chem.*, 241:1769-1777) was used to detect peracid formation. Each reaction contained MCD (0.18 mM), $H_2O_2$ (90 mM), NaBr (90 mM) in acetate buffer (1 M, pH 5.5) at 25° C. The reaction was followed spectrophotometrically at 290 nm in UV-transparent microtiter plates ($\epsilon$=19.9×10$^3$ M$^{-1}$ cm$^{-1}$).

The p-nitrophenyl acetate (pNPAc) assay contained pNPAc (0.3 mM) and 8% acetonitrile as co-solvent in BES buffer (5 mM, pH 7.2). The reaction was monitored spectrophotometrically at 404 nm ($\epsilon$=11.4·10$^3$ M$^{-1}$ cm$^{-1}$). A pH-indicator assay was used to assay substrates without inherent light absorbing properties (Janes et al., 1998, *Chem. Eur. J.* 4:2324-2331). The reactions were carried out in BES buffer (5 mM, pH 7.2) containing p-nitrophenol. As hydrolysis progresses, protons add to the p-nitrophenolate and the course of reaction can be monitored as a decrease in absorbance at 404 nm ($\epsilon$=16.5·10$^3$ M$^{-1}$ cm$^{-1}$). This provides a good estimate of reaction rates, but is limited to substrates containing only one possible acid-functionality, as several would interfere with the pH indicator. Each reaction contained substrate (5 mM), as indicated in Table 3, and 8% acetonitrile as co-solvent.

Kinetic parameters for hydrolysis of pNPAc in wild-type and Leu29Pro were carried out with pNPAc at 0.1, 0.2, 0.5, 1.0, 2.0, 4.0, and 10 mM under otherwise identical conditions as for the pNPAc-assay. Solubility problems limited higher substrate concentrations than 10 mM. Data points were fitted by non-linear regression using OriginPro 7.5 SR1 v7.5776 (OriginLab Corporation, Northampton, Mass.) with a hyperbola function of basic equation y=P1*x/(P2+x), where x is the substrate concentration (mM), P1 corresponds to $V_{max}$ (μmol min$^{-1}$ mg$^{-1}$ or U/mg), and P2 corresponds to $K_M$ (mM). $R^2$-values for were 0.992 and 0.997 for wild-type and Leu29Pro, respectively.

An estimate of kinetic parameters was also obtained for hydrogen peroxide in wild-type and Leu29Pro. The hydrogen peroxide in wild-type was 5, 10, 20, 50, 100, and 200 mM; for Leu29Pro, the concentrations were 5, 10, 20, 35, 50, 121, 152, and 200 mM. Using the basic hyperbola function, y=P1 *x/(P2+x), the $R^2$-values were 0.974 and 0.976 for wild-type and Leu29Pro, respectively.

Example 3

Enzyme Activity

The catalytic activity of the Leu29Pro mutant shifted from that of an esterase to that of a perhydrolase. Under the conditions used to assay the enzymatic activity, perhydrolase activity increased 28-fold from 0.24 to 6.8 U mg$^{-1}$ based on bromination of monochlorodimedone (see Hager et al., 1966, *J. Biol. Chem.*, 241:1769-1777). The level of perhydrolase activity in the modified esterase was higher than that of a true perhydrolase from *Pseudomonas fluorescens*, but lower than that of the perhydrolases from *Pseudomonas putida* or from *P. pyrrocinia*. In addition, the hydrolytic activity toward p-nitrophenyl acetate decreased 100-fold from 14 to 0.14 U mg$^{-1}$ (Table 1).

TABLE 1

Rate of hydrolysis and perhydrolysis for PFE variants

| PFE variant | Hydrolysis [U mg$^{-1}$][a] | $\Delta\Delta G_{mut-wt}$ [kcal mol$^{-1}$][b] | Perhydrolysis [U mg$^{-1}$][c] | $\Delta\Delta G_{mut-wt}$ [kcal mol$^{-1}$][b] |
|---|---|---|---|---|
| wild-type | 14 | 0 | 0.24 | 0 |
| Leu29Pro | 0.14 | 2.7 | 6.8 | −2.0 |
| Tyr69Met | 18 | −0.17 | 0.30 | −0.13 |
| Met95Thr | 3.4 | 0.83 | <0.02 | >1.5 |
| Asp99Glu | 8.6 | 0.28 | 0.12 | 0.44 |
| Thr122Pro | 15 | −0.062 | 0.18 | 0.17 |
| Phe227Ile | 38 | −0.60 | 0.23 | 0.050 |

[a]Hydrolase activity determined in 5 mM N,N-bis(2-hydroxyethyl)-2-aminoethanesulfonic acid (BES) buffer (pH 7.2) and 25° C. where 1 U corresponds to 1 μmol of p-nitrophenyl acetate hydrolyzed per minute;
[b]The energy equivalent of the rate change compared to wild-type PFE: $\Delta\Delta G = -RT \cdot \ln(x)$, x-fold rate-change, T = 300 K and R is the gas constant, 1 kJ mol$^{-1}$ = 4.18 kcal mol$^{-1}$; and
[c]Perhydrolase activity determined in 1 M acetate buffer (pH 5.5) where 1 U corresponds to consumption of 1 μmol of monochlorodimedon per minute at 25° C.
The error-limit is estimated to 20% in kinetic assays.

The Asp99Glu and Phe227Ile mutants showed no increase in perhydrolase activity. For Asp99Glu, both the perhydrolase activity and the hydrolysis activity were somewhat reduced compared to the wild-type (Table 1). The perhydrolase activity for Phe227Ile was statistically equivalent with the wild-type enzyme's perhydrolase activity, while the hydrolysis activity for Phe227Ile was close to three-fold higher than the hydrolysis activity of the wild-type enzyme (Table 1).

Kinetic characterizations of wild-type and Leu29Pro PFE showed that the major contributor to the observed rate-increase is a 50-fold increase in $V_{max}$ for perhydrolysis, from 0.22 to 11 U mg$^{-1}$ in the wild-type and mutant enzymes, respectively. The Leu29Pro mutation also increased the Km for hydrogen peroxide three-fold, from 17 mM to 58 mM. These values point to a 14-fold increased catalytic efficiency ($V_{max}/K_M$) for perhydrolysis of acetic acid, from 13 to 180 U mg$^{-1}$M$^{-1}$, corresponding to a lowered activation energy barrier of 1.6 kcal mol$^{-1}$ at 300 K. The Leu29Pro mutation also caused a 50-fold decrease in the $V_{max}$ for the hydrolysis of p-nitrophenyl acetate (pNPAc), while the $K_M$ increased three-fold (Table 2), altogether changing the catalytic efficiency ($V_{max}/K_M$) 165-fold corresponding to an elevated activation energy barrier for hydrolysis of 3.0 kcal mol$^{-1}$ at 300 K.

TABLE 2

Kinetic parameters for p-nitrophenyl acetate (pNPAc) and hydrogen peroxide

| Enzyme | $V_{max}$ [U mg$^{-1}$] | $K_M$ [mM] | $V_{max}/K_M$ [U mg$^{-1}$ M$^{-1}$] |
|---|---|---|---|
| Wild-type, pNPAc | 143 ± 9 | 2.8 ± 0.4 | 51000 |
| Leu29Pro, pNPAc | 2.8 ± 1.1 | 8.9 ± 1.1 | 310 |
| Wild-type, H$_2$O$_2$ | 0.22 ± 0.02 | 17 ± 4 | 13 |
| Leu29Pro, H$_2$O$_2$ | 11 ± 1 | 58 ± 12 | 180 |

The hydrolytic activity of Leu29Pro toward un-activated esters decreased much less dramatically, from no change to an eight-fold decrease (Table 3). The rate-determining step for hydrolysis may differ between activated esters (such as pNPAc) and un-activated esters. For activated esters, the acylation is likely fast and deacylation becomes rate-determining. For un-activated esters, the acylation and deacylation are more similar than for activated esters such as pNPAc. The difference between the rate of hydrolysis of activated and un-activated esters suggests that the Leu29Pro mutation slows down the hydrolysis of p-nitrophenyl acetate by slowing down the deacylation step.

TABLE 3

Rate of hydrolysis and relative rates for several ester substrates

| Ester | wild-type [U mg$^{-1}$][a] | Leu29Pro [U mg$^{-1}$][a] | x-fold decrease[b] |
|---|---|---|---|
| p-nitrophenyl acetate[c] | 14 | 0.50 | 100 |
| ethyl butyrate | 1.3 | 0.16 | 8.1 |
| ethyl valerate | 0.65 | 0.083 | 7.8 |
| propyl propionate | 0.91 | 0.18 | 5.1 |
| butyl propionate | 0.57 | 0.14 | 4.1 |
| ethyl propionate | 0.75 | 0.19 | 3.9 |
| methyl propionate | 0.38 | 0.33 | 1.2 |

[a]Specific activity of ester hydrolysis determined in 5 mM N,N-bis(2-hydroxyethyl)-2-aminoethanesulfonic acid (BES) buffer (pH 7.2) containing 0.51 mM p-nitrophenol and 5 mM substrate at 25° C. where 1 U corresponds to 1 μmol of protons generated from hydrolysis per minute;
[b]The rate of hydrolysis in wild-type PFE divided by rate of hydrolysis in Leu29Pro PFE; and
[c]Experimental value, [pNPAc] = 0.3 mM.

Example 4

Proposed Molecular Basis of New Perhydrolase Activity

Molecular modeling was used to identify the molecular basis of the increase in perhydrolase activity caused by the Leu29Pro mutation. Chain A of the crystal structure of the free PFE enzyme (PDB ID: 1V A4) was used as starting point for modeling experiments. Modeling was performed using the InsightII (Version 2000.1) software on a SGI UNIX workstation. The system was described by using the cvff force field. Non-standard partial charges of the tetrahedral intermediate were calculated with the AM1 algorithm. A formal charge of −1 was assigned to the oxyanion oxygen of the tetrahedral intermediate. A distance dependent dielectric constant of unity was used in all calculations. The catalytic His224 was defined as protonated. Energy minimization procedures were as described previously (Raza et al., 2001, *Prot. Sci.* 10.329-338). Leu29 in the wild-type structure was manually changed to cis-Pro before modeling in the tetrahedral intermediate. The tetrahedral intermediate of the deacylation step was manually modeled onto Ser94. Any water molecules near the active site were removed to make room for the substrate. After energy minimization of the whole system hydrogen bond angles, and distances between heavy atoms participating as donors or acceptors, were measured.

After minimization, an overlay of the proline residue in Leu29Pro PFE on the proline residue in CPO-F (PDB ID: 1A8S) confirmed identical conformations. Assuming that perhydrolysis takes place with an esterase-like mechanism, the second tetrahedral intermediate was modelled to represent the transition state for hydrogen peroxide attack on the acetyl-enzyme.

All modeled structures showed productive hydrogen bonds for catalytic triad residues and oxyanion-hole residues. In Leu29Pro PFE, a hydrogen bond was found between the carbonyl oxygen of Trp28 and the peroxide hydroxyl-group, having a predicted O—O distance of 2.7 Å (O—H—O angle 133°). Similarly, this hydrogen bond length in CPO-F was 2.7 Å (O—H—O angle 127°). These distances are within the typical values for a hydrogen bond from a hydroxyl-group oxygen to a carbonyl-oxygen: 2.8±0.1 Å (Schultz & Schirmer, *Principles of Protein Structure*, Springer-Verlag, New York, 1984, p. 35). In contrast, the corresponding hydrogen bond in wild-type PFE is much weaker, having a predicted O—O distance of 3.2 Å (O—H—O angle 114°).

Previous analysis of the CPO-F X-ray structure noted that Pro29 adopts a cis-peptide conformation, which may cause hydrogen peroxide to react instead of water. See, for example, Hofmann et al., 1998, *J. Mol. Biol.*, 279:889-900. There, the perhydrolase activity of CPO-F was attributed to differences in nucleophilicity between hydrogen peroxide and water. The results reported herein suggest that a hydrogen bond between the carbonyl oxygen and the peroxide nucleophile is the molecular basis for the increased perhydrolase activity. A peroxide hydroxyl-carbonyl hydrogen bond could favour the perhydrolase reaction by binding and orienting the hydrogen peroxide in a catalytically productive orientation. The energy equivalent of the rate-increase of perhydrolysis is 1.6 kcal mol$^{-1}$, which is consistent with a new hydrogen bond since a hydrogen bond between a neutral donor and neutral acceptor typically contributes 1-2 kcal mol$^{-1}$ to substrate selectivity (see, for example, Fersht et al., 1985, *Nature*, 314:235-238; and Fersht, 1988, *Biochemistry*, 27:1577-1580).

Figure 1:
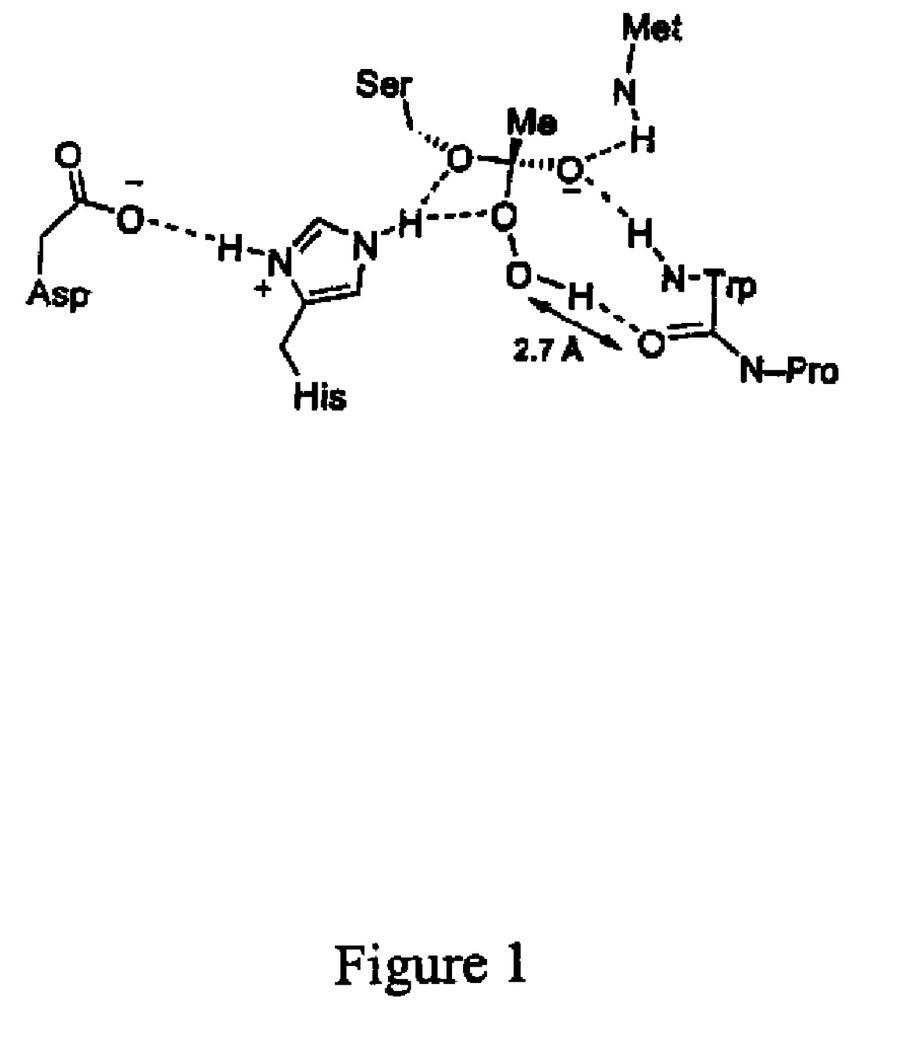
FIG. 1 is a schematic showing the proposed molecular basis of perhydrolase activity in a *Pseudomonas fluorescens* esterase. The formation of the second tetrahedral intermediate (after hydrogen peroxide attack) can be facilitated and the intermediate subsequently stabilized by an important hydrogen bond in a Leu29Pro mutant.

To identify the molecular basis of the decreased hydrolytic activity of Leu29Pro toward p-nitrophenyl acetate, the first and second tetrahedral intermediates of hydrolysis were modeled. Modeling of the first tetrahedral intermediate of hydrolysis of pNPAc showed no differences that could account for the large rate decrease. The pNP moiety does adopt different configurations in wild-type and Leu29Pro PFE, but neither structure encounters significant steric strain. See FIG. 1.

Computer modeling of the second tetrahedral intermediate showed different hydrogen bonds of the water attacking the acetyl enzyme intermediate in wild-type PFE and in the Leu29Pro mutant. In wild-type PFE, a bridging water molecule hydrogen bonds to the carbonyl group of Trp28 and to the tetrahedral intermediate ($O_i$—$O_w$-distance: 2.5 Å, $O_w$—$O_{Trp28}$-distance: 2.6 Å, angles: 166° and 172°, respectively). However, in Leu29Pro, this carbonyl group has moved ~0.5 Å closer to the water forming the tetrahedral intermediate so a bridging water molecule no longer fits, but not close enough to form a direct hydrogen bond (O—O-distance: 4.3 Å, O—H—O-angle: 139°). Without being bound by any particular mechanism, this loss of a hydrogen bond in the tetrahedral intermediate is a likely origin of the lower hydrolytic activity of the Leu29Pro mutant because this change slowed the presumably rate-limiting deacylation step.

Example 5

Modeling and Mutagenesis of Other Esterases and Lipases

The tetrahedral intermediate of perhydrolysis was modeled into CALB to verify that the model presented herein is applicable to a variety of esterases and lipases.

*Candia antarctica* lipase B (CALB; PDB ID: 1TCA): The catalytic triad residues of CALB are Ser105, His224, and Asp187. Trp28 is the oxyanion hole residue (OXY) in PFE, which corresponds to Thr40 in CALB (6.0 Å between OXY and Ser105 Oγ). The residues surrounding the OXY residue (Thr40 is shown in bold and underlined) are VPG<u>T</u>GTT. Based on the methods described herein, increased perhydrolase activity is achieved by generating a modified polypeptide containing a Gly41Pro mutation. Modeling suggests that, in fact, Gly41Pro forms a stable tetrahedral intermediate during deacylation, implying a good perhydrolase activity.

*Humicola lanuginosa* lipase (HLL; PDB ID: 1DT5): The catalytic triad residues of HLL are Ser146, His258, and Asp201. As indicated above, Trp28 is the oxyanion hole residue (OXY) in PFE, which corresponds to Ser85 in HLL (6.3 Å between OXY and Ser146 Oγ). The residues surrounding the OXY residue (Ser85 is shown in bold and underlined) are FRG<u>S</u>RSIG. Based on the methods described herein, increased perhydrolase activity is achieved by generating a modified polypeptide containing an Arg86Pro mutation.

*Pseudomonas cepacia* lipase (PCL; PDB ID; 1OIL): The catalytic triad residues of PCL are Ser87, His286, and Asp264. As indicated above, Trp28 is the oxyanion hole residue (OXY) in PFE, which corresponds to Leu17 in PCL (6.4 Å between OXY and Ser87 Oγ). The residues surrounding the OXY residue (Leu17 in shown in bold and underlined) are VHG<u>L</u>TGT. Based on the methods described herein, increased perhydrolase activity is achieved by generating a modified polypeptide containing a Thr18Pro mutation.

*Candida rugosa* lipase (CRL; PDB ID: 1GZ7): The catalytic triad residues of CRL are Ser209, His449, and Glu341. As indicated above, Trp28 is the oxyanionic hole residue in PFE, which corresponds to Gly124 in CRL (7.6 Å between OXY and Ser209 Oγ). The residues surrounding the OXY residue (Gly124 is shown in bold and underlined) are FGG<u>G</u>FGL. Because CRL has a GGGX motif, the loop conformation is slightly different than the previous lipases. Based on the methods described herein, increased perhydrolase activity is likely achieved by generating a modified polypeptide containing a Phe125Pro mutation. In the CRL open form (PDB ID: 1CRL), the distance between OXY and Ser209 Oγ is 6.7 Å.

*Bacillus* lipase: The catalytic triad residues of *Bacillus* lipase are Ser118 and His363, apparently without the third Asp/Glu residue. Based on the modeling, Asp322 is H-bonded to the amide of His363. The oxyanion hole residue (OXY) of *Bacillus* lipase is Phe21. Based on modeling, Thr22 is hydrogen bonded to His19, presumably to help stabilize the loop. Mutating Thr22Pro may twist the carbonyl oxygen of interest 180 deg to hydrogen bond a putative tetrahedral intermediate of perhydrolysis. The residues surrounding the OXY residue (Phe21 is shown in bold and underlined) are Leu18 His19 Gly20<u>Phe21</u> Thr22 Gly23 Trp24. Based on the methods described herein, increased perhydrolase activity is likely achieved by generating a modified polypeptide containing a Thr22Pro mutation.

Example 6

Sequences

```
SEQ ID NO:1
GATCTGGACGTCCTCGGCCCCCGGCGCGCGGCGTCGAAGGTGAAGGGCTT

GAGGGCATCCTTGGCGTTCTGGGCGGCGTAGCTGTAAGTCTTGGCCATTT

CGTTCACCTGTGTGATCTGACGGTAGAGGTCAGTGGACCAGCATAGACGC

TGAACCGTTCAACCGAGCACACCGGTACAAGCCCTTCGTCCGGTTTCACG

CAATAGTGCGCTAGAGTCTTTCAGCCCCCTCAACCAGGAGTTTTTGCATG

AGCACATTTGTTGCAAAAGACGGTACCCAGATCTATTTCAAGGACTGGGG

CAGCGGTAAACCGGTGTTGTTCAGCCACGGTTGGCTACTGGATGCCGACA

TGTGGGAATACCAGATGGAGTACCTCAGCAGCCGCGGCTATCGCACCATC

GCCTTTGACCGCCGCGGCTTTGGCCGCTCGGACCAACCCTGGACCGGCAA

CGACTACGACACCTTCGCCGACGACATCGCCCAGTTGATCGAACACCTGG

ACCTCAAGGAGGTGACCCTGGTGGGCTTCTCCATGGGCGGCGGCGATGTG

GCCCGCTACATCGCCCGCCACGGCAGCGCACGGGTGGCCGGCCTGGTGCT

GCTGGGCGCCGTCACCCCGCTGTTCGGCCAGAAGCCCGACTATCCGCAGG

GTGTCCCGCTCGATGTGTTCGCAAGGTTCAAGACTGAGCTGCTGAAGGAT

CGCGCGCAGTTCATCAGCGATTTCAACGCACCGTTCTATGGCATCAACAA

GGGCCAGGTCGTCTCCCAAGGCGTGCAGACCCAGACCCTGCAAATCGCCC

TGCTGGCCTCGCTCAAGGCCACGGTGGATTGCGTCACCGCGTTCGCCGAA

ACCGACTTCCGCCCGGACATGGCCAAGATCGACGTACCCACCCTGGTGAT
```

-continued

CCATGGCGATGGCGACCAGATCGTGCCGTTCGAGACCACCGGCAAAGTGG

CGGCGGAGTTGATCAAGGGCGCCGAACTGAAGGTGTACAAGGACGCGCCC

CACGGGTTCGCGGTGACCCACGCCCAGCAGTTGAACGAAGACCTGTTGGC

GTTCTTGAAACGCTGAGTTAATGTCTGCCTTTATCGGCCGGGCTTGCCCG

GCCTTTTTTTTACGCGCTCGAATCTCGCGCGGTCGCCGGGCACGATCGTG

CTGAACCGCCGCCCCCTCGCCACGGTCCCAACCCATACGTTCATCGCTGC

AG

SEQ ID NO:3
MSTFVAKDGTQIYFKDWGSGKPVLFSHGWLLDADMWEYQMEYLSSRGYRT

IAFDRRGFGRSDQPWTGNDYDTFADDIAQLIEHLDLKEVTLVGFSMGGGD

VARYIARHGSARVAGLVLLGAVTPLFGQKPDYPQGVPLDVFARFKTELLK

DRAQFISDFNAPFYGINKGQVVSQGVQTQTLQIALLASLKATVDCVTAFA

ETDFRPDMAKIDVPTLVIHGDGDQIVPFETTGKVAAELIKGAELKVYKDA

PHGFAVTHAQQLNEDLLAFLKR

SEQ ID NO:2
ATGAAGCTACTCTCTCTGACCGGTGTGGCTGGTGTGCTTGCGACTTGCGT

TGCAGCCACTCCTTTGGTGAAGCGTCTACCTTCCGGTTCGGACCCTGCCT

TTTCGCAGCCCAAGTCGGTGCTCGATGCGGGTCTGACCTGCCAGGGTGCT

TCGCCATCCTCGGTCTCCAAACCCATCCTTCTCGTCCCCGGAACCGGCAC

CACAGGTCCACAGTCGTTCGACTCGAACTGGATCCCCCTCTCAACGCAGT

TGGGTTACACACCCTGCTGGATCTCACCCCCGCCGTTCATGCTCAACGAC

ACCCAGGTCAACACGGAGTACATGGTCAACGCCATCACCGCGCTCTACGC

TGGTTCGGGCAACAACAAGCTTCCCGTGCTTACCTGGTCCCAGGGTGGTC

TGGTTGCACAGTGGGGTCTGACCTTCTTCCCCAGTATCAGGTCCAAGGTC

GATCGACTTATGGCCTTTGCGCCCGACTACAAGGGCACCGTCCTCGCCGG

CCCTCTCGATGCACTCGCGGTTAGTGCACCCTCCGTATGGCAGCAAACCA

CCGGTTCGGCACTCACCACCGCACTCCGAAACGCAGGTGGTCTGACCCAG

ATCGTGCCCACCACCAACCTCTACTCGGCGACCGACGAGATCGTTCAGCC

TCAGGTGTCCAACTCGCCACTCGACTCATCCTACCTCTTCAACGGAAAGA

ACGTCCAGGCACAGGCCGTGTGTGGGCCGCTGTTCGTCATCGACCATGCA

GGCTCGCTCACCTCGCAGTTCTCCTACGTCGTCGGTCGATCCGCCCTGCG

CTCCACCACGGGCCAGGCTCGTAGTGCAGACTATGGCATTACGGACTGCA

ACCCTCTTCCCGCCAATGATCTGACTCCCGAGCAAAAGGTCGCCGCGGCT

GCGCTCCTGGCGCCGGCAGCTGCAGCCATCGTGGCGGGTCCAAAGCAGAA

CTGCGAGCCCGACCTCATGCCCTACGCCCGCCCCTTTGCAGTAGGCAAAA

GGACCTGCTCCGGCATCGTCACCCCCTGA

SEQ ID NO:4
LPSGSDPAFSQPKSVLDAGLTCQGASPSSVSKPILLVPGTGTTGPQSFDS

NWIPLSTQLGYTPCWISPPPFMLNDTQVNTEYMVNAITALYAGSGNNKLP

VLTWSQGGLVAQWGLTFFPSIRSKVDRLMAFAPDYKGTVLAGPLDALAVS

APSVWQQTTGSALTTALRNAGGLTQIVPTTNLYSATDEIVQPQVSNSPLD

SSYLFNGKNVQAQAVCGPLFVIDHAGSLTSQFSYVVGRSALRSTTGQARS

ADYGITDCNPLPANDLTPEQKVAAAALLAPAAAAIVAGPKQNCEPDLMPY

ARPFAVGKRTCSGIVTP

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of increasing perhydrolase activity in an esterase, comprising:
providing a nucleic acid encoding the esterase, wherein the nucleic acid encoding the esterase has the sequence shown in SEQ ID NO:1;
modifying one or more nucleotides in the codon encoding the OXY+1 residue in the esterase to nucleotides that cause said codon to encode an amino acid which can adopt a cis configuration at the carbon-nitrogen peptide bond; and
expressing the modified nucleic acid to generate a modified polypeptide, wherein the modified polypeptide has increased perhydrolase activity compared to the pre-modified esterase.

2. The method of claim 1, further comprising:
screening the unmodified esterase for perhydrolase activity.

3. The method of claim 1, further comprising:
screening the modified polypeptide for perhydrolase activity.

4. The method of claim 1, wherein the amino acid that can adopt a cis-configuration at the carbon-nitrogen peptide bond is proline or a derivative of proline.

5. The method of claim 4, wherein the proline derivative is hydroxyproline.

6. A method of introducing perhydrolase activity into an esterase comprising:
providing a nucleic acid encoding the esterase, wherein the nucleic acid encoding the esterase has the sequence shown in SEQ ID NO:1;
modifying one or more nucleotides in the codon encoding the OXY+1 residue in the esterase to nucleotides that cause said codon to encode an amino acid which can adopt a cis-configuration at the carbon-nitrogen peptide bond; and
expressing the modified nucleic acid to generate a modified polypeptide, wherein the modified polypeptide has perhydrolase activity.

7. A method of converting a polypeptide having predominantly esterase activity to a polypeptide having predominantly perhydrolase activity, comprising:
provi ding a nucleic acid encoding the polypeptide having predominantly esterase activity, wherein the nucleic acid encoding the polypeptide having predominantly esterase activity has the sequence shown in SEQ ID NO:1;
modifying one or more nucleotides in the codon encoding the OXY+1 residue in the polypeptide to nucleotides that cause said codon to encode an amino acid which can adopt a cis configuration at the carbon-nitrogen peptide bond; and
expressing the modified nucleic acid to generate a modified polypeptide, wherein the modified polypeptide has predominantly perhydrolase activity.

* * * * *

UNITED STATES PATENT AND TRADEMARK OFFICE
CERTIFICATE OF CORRECTION

PATENT NO. : 7,384,787 B2
APPLICATION NO. : 11/422188
DATED : June 10, 2008
INVENTOR(S) : Romas Kazlauskas It is certified that error appears in the above-identified patent and that said Letters Patent is hereby corrected as shown below:

Title Page, line 25, col. 2, References Cited, Other Publications, Drabloøs et al. reference, please delete "Drabloøs" and insert --Drabløs-- therefor;

Title Page, Abstract, line 1, please delete "n" and insert --an-- therefor;

Column 20, line 54 (Claim 6), please delete "esterase" and insert --esterase,-- therefor;

Column 20, line 61 (Claim 6), please delete "which" and insert --that-- therefor.

Signed and Sealed this

Eleventh Day of August, 2009

David J. Kappos
*Director of the United States Patent and Trademark Office*